United States Patent [19]
Tanaka et al.

[11] Patent Number: 6,090,610
[45] Date of Patent: Jul. 18, 2000

[54] MACROLIDE COMPOUND 0406

[75] Inventors: Yasushi Tanaka; Hisayuki Komaki; Yuzuru Mikami; Katsukiyo Yazawa, all of Chiba-ken; Jun'ichi Kobayashi, Hokkaido, all of Japan

[73] Assignee: Higeta Shoyu Co., Ltd., Tokyo, Japan

[21] Appl. No.: 09/239,812

[22] Filed: Jan. 29, 1999

Related U.S. Application Data

[62] Division of application No. 08/847,413, Apr. 24, 1997, Pat. No. 6,004,995.

[30] Foreign Application Priority Data

Apr. 30, 1996 [JP] Japan ................................ 8-130633

[51] Int. Cl.[7] .............................. C12N 1/20; C12P 19/58; A01N 43/02
[52] U.S. Cl. ......................... 435/252.1; 435/77; 435/72; 514/449; 536/6.5
[58] Field of Search ................... 435/252.1, 77, 435/872; 514/449; 536/6.5

[56] References Cited

PUBLICATIONS

Borel et al, "Biological Effects of Cyclosporin A: A New Antilymphyoctic Agent", *Agents and Actions* 6(4):468–475 (19976).

Kino et al, "FK–506, A Novel Immunosuppressant Isolated From a Streptomyces", *J. Antibiotics* XL(9):1249–1255 (1987).

Kumagai et al, "PC–766B, A New Macrolide Antibiotic Produced by *Nocardia brasiliensis*", *J. Antibiotics* 46(7):1139–1144 (1993).

Mikami et al, "Susceptibility Patterns of Pathogenic Nocardia to Some Selected Antimicrobial Agents and Their Usefulness in the Identification Work in a Clinical Laboratory", *Bull. JFCC* 5:89–95 (1989).

Shigemori et al, "Brasilinolide A, New Immunosuppressive Macrolide from Actinomycete *Nocardia brasiliensis*", *Tetrahedron* 52(27):9031–9034 (1996).

Primary Examiner—Herbert J. Lilling
Attorney, Agent, or Firm—Browdy and Neimark

[57] ABSTRACT

Compound 0406 having a chemical structural formula represented by the chemical formula (1) below and having an excellent immuno suppressive activity, and pharmaceutically acceptable salts thereof.

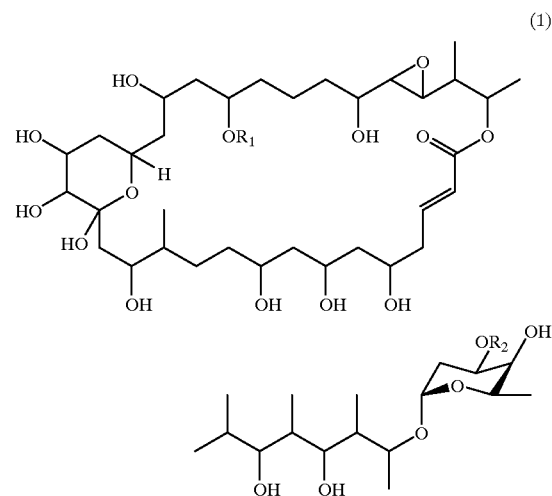

(wherein $R_1$ is $-COCH_2COOH$ or H; $R_2$ is $-CO(CH_2)_3CH_3$ or $-CO(CH_2)_4CH_3$ or H.)

8 Claims, 2 Drawing Sheets

MACROLIDE COMPOUND 0406

CROSS-REFERENCE TO RELATED APPLICATIONS

This is a division of parent application Ser. No. 08/847,413, filed Apr. 24, 1997, now U.S. Pat. No. 6,004,995 the entire contents of which are hereby incorporated by reference.

DETAILED DESCRIPTION OF THE INVENTION

1. Field of the Invention

The present invention relates to a novel compound 0406, a process for production of the compound, microorganisms producing compound 0406 and the use thereof. Compound 0406 is a novel macrolide compound, conventionally unkown, isolated and purified from the culture of microorganisms, particularly actinomycetes, and the compound has excellent biological activities, particularly an immuno suppressive activity.

Thus, the novel macrolide compound of the present invention may effectively be used as an immuno suppressive agent, for example for suppressing rejection during organ transplantation or dermal transplantation or as a preventive agent and/or a therapeutic agent for auto-immune diseases.

2. Prior Art

A variety of immuno suppressive agents has been used in recent years for a series of conditions called as allergic diseases, erythematoses, auto-immune diseases or connective tissue diseases and have drawn attention of their effects. Similarly, such agents have been used for suppressing rejection for transplanting organs such as liver, heart, and kidney. The significance thereof has increased gradually year after year.

Cyclosporin A has been developed as an agent with higher specificity and great selectivity to a group of immune cells in this field (J. F. Borel et al., Agents and Actions, Vol.6, pp.468–475 (1976)); Cyclosporin A suppresses the generation of interleukin-2 (IL-2) from helper T-cells with no suppression of suppresser T-cells, so that it is demonstrated that Cyclosporin A prevents graft rejection. Thus, the agent has attained prominent outcome in organ transplantation such as kidney or myeloma transplantation, so the agent is now used clinically.

It is noted however that the agent has side effects such as acute kidney toxicity, mild neurological disorders, and periodontic hyperplasia disadvantageously in some cases.

A macrolide antibiotic tacrorims (FK506) discovered in 1984 (T. Kino et al., J. Antibiot., Vol.40, pp.1249–1255 (1987)) has achieved preferable outcome as an immuno suppressive agent. However, tacrorims has drawbacks such as low productivity because tacrorims-related substances of a trace amount are also generated as byproducts in the cultivation of the microorganisms, so the productivity should be improved. Therefore, such drawbacks may potentially work as a regulating condition of future progress thereof. Furthermore, the agent is also deleterious in the pancreas and the kidney and its action is similar to that of Cyclosporin A. Hence, a novel safer agent with a different action has been desired strongly.

Problems to be Solved by the Invention

So as to satisfy such demands in the industries, the present invention has been achieved for the object of developing a far better novel agent than conventionally known substances.

Means for Solving the Problems

For the purpose of developing a novel immuno suppressive agent with more effective immuno suppressive activity, the present inventors have made wide investigations of natural substances, specifically microbial metabolites. consequently, the inventors have found that a novel bacterial strain Nocardia brasiliensis IFM 0406 (FERM BP-5498) produces an objective substance in the culture broth. Then, the inventors have made detailed investigations of the physico-chemical properties of the substance and determined its chemical structure. It has been verified that the substance is a novel substance conventionally unknown. As described below, the substance is a novel substance represented by the formula (1), wherein a 32-membered macrolide compound with epoxides is bonded with deoxyfucose. This has been designated compound 0406.

More specifically, the present invention relates to the novel compound 0406 having the formula (1), and pharmaceutically acceptable salts thereof.

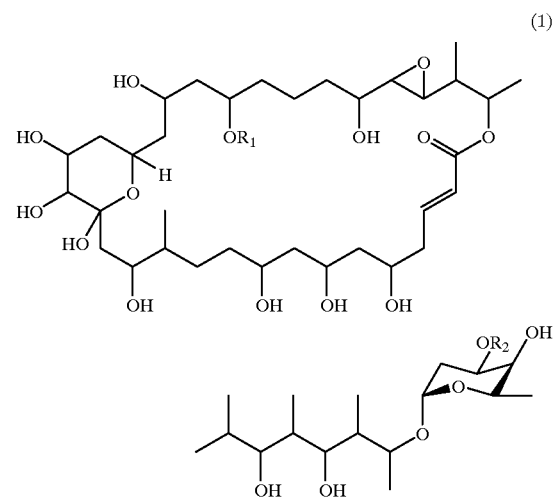

(1)

(wherein $R_1$ is —$COCH_2COOH$ or H; $R_2$ is —$(CH_2)_3CH_3$ or —$CO(CH_2)_4CH_3$ or H.)

The present invention furthermore relates to a novel immuno suppressive agent containing the novel macrolide compound 0406 or a pharmaceutically acceptable salt thereof as the effective compound. The present invention will now be described below.

EMBODIMENTS OF THE INVENTION

Compound 0406 of the present invention includes six compounds A, B, C, D, E and F, separated so far. Among these compounds, compound 0406-A is a compound represented by the formula (1), wherein $R_1$ is —$COCH_2COOH$ and $R_2$ is —$CO(CH_2)_3CH_3$. The physico-chemical properties thereof are as shown in Tables 1 and 2.

Table 1

Physico-chemical Properties of Compound 0406-A (1) Color and state of the substance; white powder.
(2) Specific rotation: $[\alpha]^{28}_D$:-27.4 (1% methanol).
(3) Infra red absorption spectrum: significant signals as shown below;

$\nu^{KBr}_{max}$ = 3400, 1740, 1700, 1640, 1580, cm$^{-1}$.

(4) Ultraviolet absorption spectrum: significant signals as shown below;

$\lambda^{MeOH}_{max}$ = 214 ($\epsilon$ 14900) nm (E$^{1\%}_{1\ cm}$).

Figure 1:
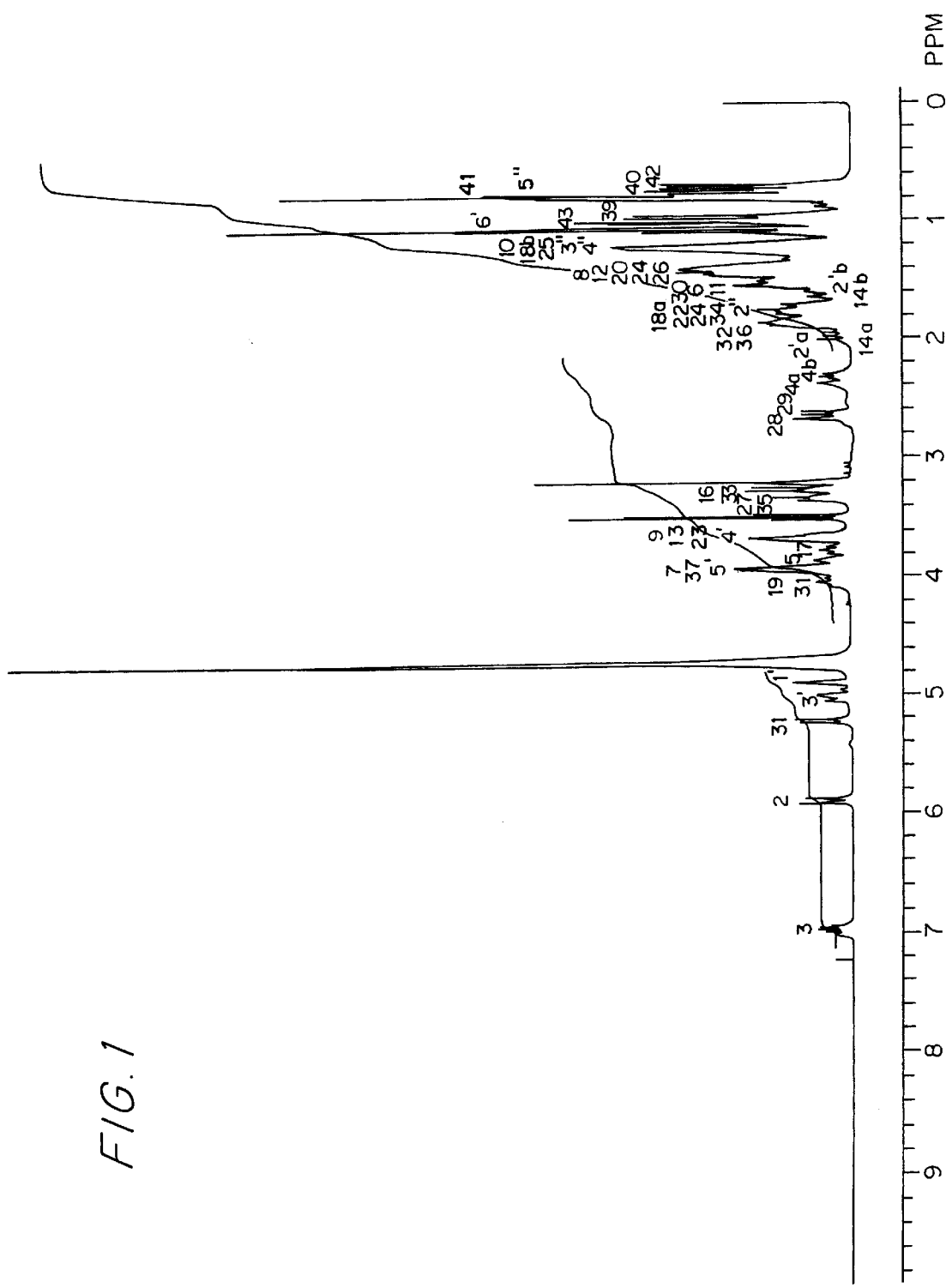
FIG. 1 shows $^1H$-NMR spectrum ($CD_3OD$) of the compound 0406-A.
Figure 2:
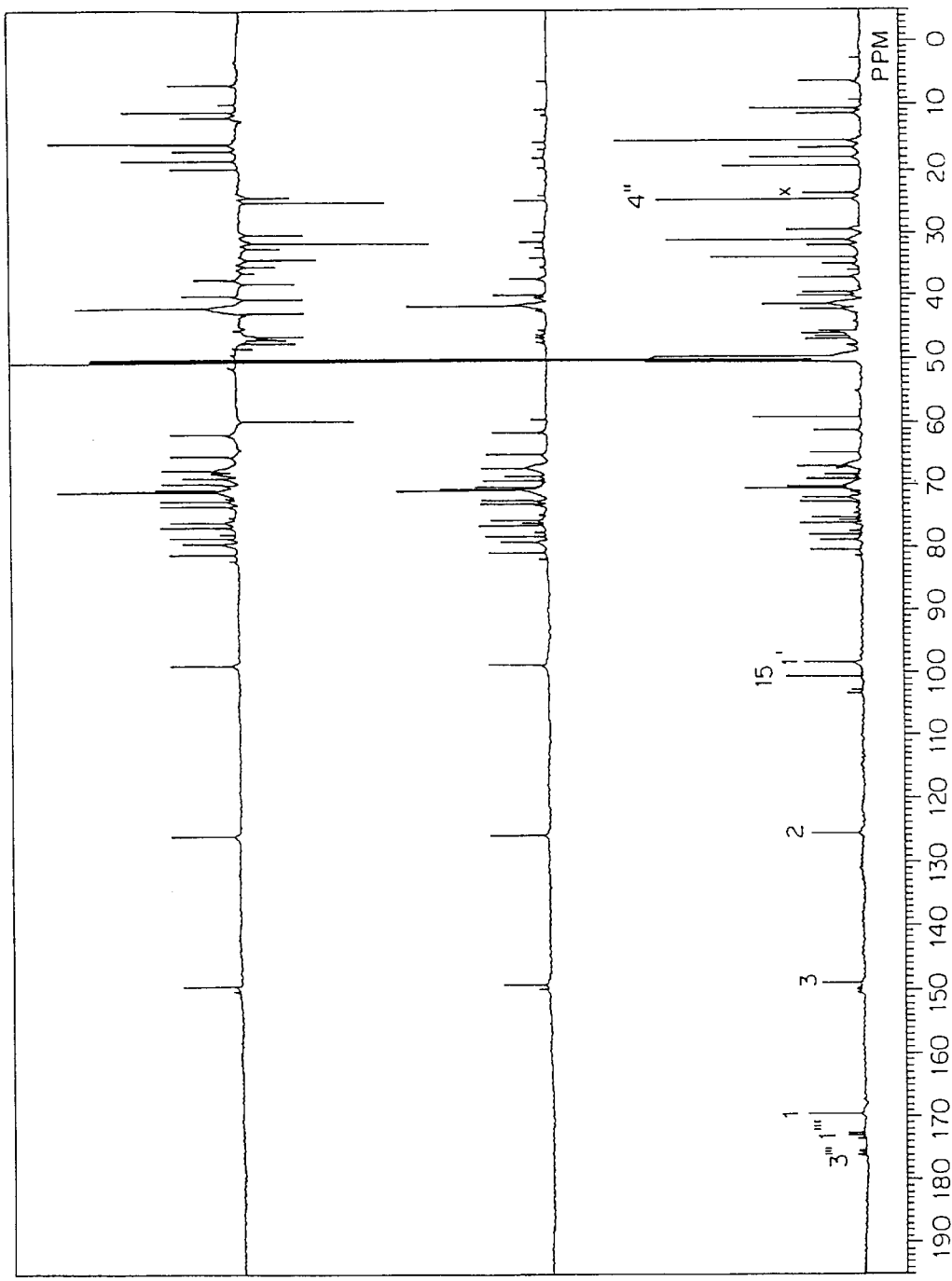
FIG. 2 shows $^{13}C$-NMR spectrum ($CD_3OD$) of the compound 0406-A.

(5) Molecular formula and FAB-MS: Molecular formula: $C_{57}H_{98}O_{24}$. FAB-MS m/z: 1189 (M+Na)+HR-FAB-MS m/z: 11890.6403 (M+Na)$^+$.
(6) $^1$H -NMR spectrum (FIG. 1): significant signals as shown in Table 2.
(7) $^{13}$C-NMR spectrum (FIG. 2): significant signals as shown in Table 2.
(8) Solubility: Soluble in water, methanol, ethanol and DMSO. Insoluble in chloroform, ethyl acetate and ether.

TABLE 2

$^1$H—NMR and $^{13}$C—NMR (CD$_3$OD) data of 0406-A

| position | $^1$H$^a$ J(Hz) | $^{13}$C$^a$ | HMBC($^1$H) |
|---|---|---|---|
| 1 |  | 168.49 s | 2, 3, 31 |
| 2 | 6.05 d 15.6 | 124.64 d | 4 |
| 3 | 7.11 dt 15.6, 7.3 | 148.19 d | 2 |
| 4 | 2.52 m | 41.21 t | 2, 3 |
| 5 | 4.00 m | 69.72 d | 3, 4', 6 |
| 6 | 1.67 m | 45.95 t |  |
| 7 | 4.05 m | 69.10 d | 6, 8 |
| 8 | 1.56 m | 45.09 t |  |
| 9 | 3.82 m | 69.56 d | 8, 10 |
| 10 | 1.34 m | 38.98 t |  |
| 11 | 1.67 m | 33.91 t | 9, 38 |
| 12 | 1.57 m | 40.42 d | 38 |
| 13 | 3.82 m | 71.18 d | 14, 38 |
| 14 | 2.00 m, 1.94 m | 44.94 t | 16 |
| 15 |  | 99.79 s | 14a, 14b, 19 |
| 16 | 3.39 d 9.3 | 77.09 d | 17 |
| 17 | 3.93 m | 69.41 d | 16, 18a, 18b |
| 18 | 1.94 m | 41.03 t |  |
| 19 | 4.17 m | 65.49 d | 18', 20 |
| 20 | 1.57 m | 40.33 t |  |
| 21 | 4.20 m | 66.12 d | 20, 22 |
| 22 | 1.94 m, 1.91 m | 44.79 t |  |
| 23 | 3.77 m | 70.65 d | 22b |
| 24 | 1.55 m | 36.02 L |  |
| 25 | 1.38 m | 30.75 L |  |
| 26 | 1.55 m | 36.02 L |  |
| 27 | 3.44 m | 71.02 d | 28 |
| 28 | 2.78 brd 2.0 | 63.83 d |  |
| 29 | 2.76 dd 6.3, 2.0 | 60.41 d | 31, 39 |
| 30 | 1.64 m | 40.42 d | 29, 31, 39 |
| 31 | 5.36 d, 10.3 | 75.21 d | 33, 39, 40 |
| 32 | 1.89 m | 38.54 d | 31, 33, 40 |
| 33 | 3.42 m | 77.77 d | 31, 32, 40, 41 |
| 34 | 1.84 m | 36.20 d | 33, 35, 41 |
| 35 | 3.51 m | 79.60 d | 33,41.42 |
| 36 | 2.01 m | 40.42 d | 35, 42, 43 |
| 37 | 4.09 m | 74.40 d | 35, 42, 43, 1' |
| 38 | 0.96 d 7.0 | 14.42 q |  |
| 39 | 1.11 d 7.0 | 14.47 q | 39, 31 |
| 40 | 0.89 d 7.0 | 9.43 q | 31, 32 |
| 41 | 0.94 d 7.0 | 5.09 q | 34 |
| 42 | 0.86 d 7.0 | 10.14 q | 36, 37 |
| 43 | 1.16 d 7.0 | 15.62 q |  |
| 1' | 5.04 s | 97.56 d | 5' |
| 2' | 2.14 m, 1.76 m | 30.91 t | 4' |
| 3' | 5.15 m | 71.79 d | 1', 2'a, 2'b, 4' |
| 4' | 3.77 m | 69.72 d | 2'a, 5', 6' |
| 5' | 4.07 m | 68.15 d | 1',4' |

TABLE 2-continued $^1$H—NMR and $^{13}$C—NMR (CD$_3$OD) data of 0406-A

| position | $^1$H$^a$ J(Hz) | $^{13}$C$^a$ | HMBC($^1$H) |
|---|---|---|---|
| 6' | 1.24 d 7.0 | 17.05 q | 5' |
| 1" |  | 171.64 s | 3' |
| 2" | 1.36 m | 32.74 t |  |
| 3" | 1.4 m | 28.54 t |  |
| 4" | 1.36 m | 23.60 t | 5" |
| 5" | 0.95 t 7.0 | 14.42 q |  |
| 1"' |  | 172.23 s | 23 |
| 2"' | 3.39$^b$ s | 45.51 t |  |
| 3"' |  | 174.82 s |  |

$^a$δ in ppm
$^b$in DMSO-d$_6$

By FAB-MS and HR-FAB-MS, the compounds B, C, D, E, and F are analyzed of their molecular weights, to individually deduce the molecular formulas. Thus, the possible structural formulas are shown in the results below as described in claims.

0406-B:$C_{52}H_{90}O_{23}$(1082)

0406-C:$C_{54}H_{96}O_{21}$(1080)

0406-D:$C_{49}H_{88}O_{20}$(996)

0406-E:$C_{58}H_{100}O_{24}$(1180)

0406-F:$C_{55}H_{98}O_{21}$(1094)

Compound 0406 of the present invention is, for example, produced by a novel strain *Nocardia brasiliensis* IFM 0406 (FERM BP-5498).

The microbiological characteristics of the strain *Nocardia brasiliensis* IFM 0406 is as follows; morphologically, the strain has long, branched hyphae and aerial hyphae such as those observed in a species of actinomycetes when cultured in an oatmeal-agar medium (ISP No.3). By prolonging the culture duration, a number of spores were observed on the tip of the aerial hyphae; furthermore, the fragmentation of the vegetative hyphae was observed. Morphologically, the strain is concluded to belong to the genus Nocardia due to the fragmentation of the vegetative hyphase observed.

The culture and physiological characteristics of the strain *Nocardia brasiliensis* IFM 0406 in a variety of culture media are shown in Tables 3 and 4, respectively, below.

TABLE 3

Culture Characteristics of *Nocardia brasiliensis* IFM 0406

| Culture medium | Properties |
|---|---|
| ISP-2 (yeast malt agar) | vigorous growth, wrinkle on surface, pale yellow earth color |
| ISP-3 (oatmeal agar) | moderate growth, smooth surface, white yellow, virulent aerial hyphae in white |
| ISP-4 (starch/inorganic salts agar) | almost no growth |
| ISP-5 (glycerol-asparagine agar) | moderate growth, smooth surface, gray, a trace of aerial hyphae |
| ISP-6 (peptone-yeast agar) | vigorous growth, wrinkle on surface, pale brown |
| BHI (brain heart infusion agar) | vigorous growth, wrinkle on surface, pale yellow earth color |

TABLE 3-continued

Culture Characteristics of *Nocardia brasiliensis* IFM 0406

| Culture medium | Properties |
| --- | --- |
| SDA (Sabouraud agar) | vigorous growth, wrinkle on surface, pale yellow, a trace of aerial hyphae |

TABLE 4

Physiological Characteristics of *Nocardia brasiiiensis* IFM 0406

| Decomposition | |
| --- | --- |
| adenine | positive |
| caseiti | positive |
| hypoxanthine | positive |
| tyrosine | positive |
| xanthine | negative |
| Acid formation from sugar | |
| galactose | negative |
| glucose | positive |
| inositol | positive |
| ramnose | negative |
| maltose | negative |
| adonitol | negative |
| arabinose | negative |
| erythritol | positive |
| mannose | negative |
| sorbitol | negative |
| Citrate utilization | positive |
| Sensitivity against antibiotics | |
| imipenem | negative |
| tobramycin | positive |
| kanamycin | negative |
| 5-FU | negative |
| β-Lactamase formation | positive |
| Growth limit temperature | no growth at 45° C. |

The strain was cultured in a culture medium (brain heart infusion containing 2% glucose) at 30° C. with shaking at 250 rpm for 72 hours, and the cells grown in the medium were collected by centrifuge at 3,000 rpm for 10 minutes, which were then washed twice in distilled water. Further, the cells were washed in ethanol and subsequently dried in vacuum to give the dry cells. According to Bergey's Manual of Determinative Bacteriology, the 9-th edition, Williams & Willkins, Baltimore, 1993, the amino acid composition, sugar composition and lipid composition of the dry cells were determined. Meso-diamino pimelic acid was detected by the amino acid analysis, while arabinose and galactose were detected by the sugar analysis. Also, the presence of mycolic acid was determined by the lipid analysis, and the type of the acid was Nocardia type. MK-8(H4) cycle was confirmed as a principal component of the isoprenoid quinone which is a part of the bacterial lipid, while as the trace components, MK-8(H4), MK-8(H), and MK-9(H2) were confirmed. Based onthe decomposition of adenine, casein, hypoxanthine and tyrosine and additionally on the formation patterns of acids from sugar and the antimicrobial sensitivity patterns, shown in Table 4 (Mikami & Yazawa, Susceptibility pattern of pathogenic Nocardia to some selected antimicrobial agents and their usefulness in the identification work in a clinical laboratory: BuLL. JFCC, 5: 89, 1989), the bacterial strain was identified as the species *N. brasiliensis*. The results of the analysis of the G+C content and DNA homology support strongly that the strain is *N. brasiliensis*.

TABLE 5

G + C content and DNA homology of *N. brasiliensis* IFM0406

| Strain | G + C content (mol %) | DNA homology (%) | | |
| --- | --- | --- | --- | --- |
| | | A | B | C |
| A | 68.1 | 100 | NT | 100 |
| B | 69.0 | NT | 100 | 25 |
| C | 68.0 | 94 | 8 | 100 |

A: *Nocardia brasiliensis* IFM 0236T
B: *Nocardia transvalensis* IFM 0333T
C: *N. brasiliensis* IFM 0406

As shown above, because the strain is classified as *Nocardia brasiliensis* and characteristically produces compound 0406, the strain was designated as *Nocardia brasiliensis* IFM 0406 as a new strain, which was then internationally deposited at the National Institute of Bioscience and Human-Technology, Agency of Industrial Science and Technology in Japan under No. FERM BP-5498 on Apr. 3, 1996.

Thus, the present invention relates to a novel strain *Nocardia brasiliensis* IFM 0406 producing the novel compound 0406 represented by the formula (1).

Compound 0406 of the present invention is produced by the novel bacterial strain *N. brasiliensis* IFM 0406 (FERM BP-5498). Also, it has been confirmed that the compound may be produced by other strains belonging to the genus Nocardia, for example *Nocardia transvalensis*. The production of compound 0406 is not limited to these microorganisms.

Still furthermore, the present invention encompasses the use of a variety of all variants capable of producing compound 0406, including artificial variants generated from these organisms by X-ray irradiation, ultraviolet irradiation, gamma irradiation, and other mutagenesis treatments with nitrogen mustard, N-methyl-N'-nitro-N-nitrosoguanidine, 2-aminopurine, and ethyl methane sulfonate, as well as spontaneous variants.

The novel compound 0406 represented by the formula (1), in accordance with the present invention, may be produced by organisms as described above, other than by chemical synthesis.

In the former case, the novel compound 0406 represented by the formula (1) in accordance with the present invention may be produced by bacteria of the genus Nocardia, capable of producing the compound; for example, the compound may be produced by culturing *Nocardia brasiliensis* IFM 0406 in a culture medium containing carbon sources and nitrogen sources which are decomposable by IFM 0406, preferably under aerobic submerged-culture conditions (for example, shaking culture and aeration agitation culture by a fermentor and the like).

As the carbon sources, preferably, use may be made of glucose, glycerol, sucrose, starch, dextrin and other carbohydrates.

As the nitrogen sources, preferably, use may be made of oatmeal, yeast extract, beef extract, tuna meat extract, peptone, gluten meal, cotton seed powder, soybean meal, corn steep liquor, dryyeast, wheat germ, peanutpowder, chickenbone meat meal and the like; additionally, use may be made of inorganic and organic nitrogen compounds such as ammonium salts (for example, ammonium nitrate, ammonium sulfate, ammonium phosphate and the like), urea, and amino acids, advantageously.

Advantageously, these carbon sources and nitrogen sources may be used in combination, but not necessarily pure such products may be used. Impure such products may contain growth factors and trace elements, which may be preferably used.

If necessary, inorganic salts may be added to the culture medium, such as sodium carbonate, potassium carbonate, sodium phosphate, potassium phosphate, sodium chloride, potassium chloride, sodium iodide, potassium iodide, magnesium salts, copper salts, cobalt salts and the like.

If necessary and specifically if the culture medium is foaming, an antifoaming agent including liquid paraffin, animal oil, vegetable oil, mineral oil, silicone and the like may be added.

So as to industrial production of the objective substance on a large scale, aeration-agitation culture may be preferably carried out, like other fermentation products. On a small scale production, culturing in flasks with shaking may be preferable.

For culturing in a large tank, so as to prevent the delay of bacterial growth at the process of producing compound 0406, the bacterium is firstly inoculated and cultured in a relatively small volume of the culture medium, and the culture is then transferred into a large production tank to be cultured therein to produce the compound.

In this case, the compositions of the culture media for pre-culture and for production culture may be the same or different from each other if necessary.

Culturing may be preferably carried out with aeration and agitation; known processes may be used appropriately, for example agitation by means of propeller or other machines, rotation or shaking of fermenter, pump treatment, aeration and the like. Preferably, air for aeration may be sterilized preliminarily.

Cultivation temperature may be appropriately modified within a range in which the bacteria capable of producing compound 0406 can produce the compound; generally, the temperature is 10 to 40° C., preferably 25 to 35° C.

Cultivation time depends on the culture conditions and culture volume, but generally, the time is about one day to one week.

After completion of fermentation, the objective compound 0406 is recovered from the culture. More specifically, the cells are subjected to direct extraction with water and/or an organic solvent, or mechanical pulverizing or pulverizing by known means such as ultrasonication followed by extraction with water and/or an organic solvent, and subsequent recovery and purification by known methods. The culture broth may be extracted directly with a solvent or may be subjected to filtration or centrifuge, subsequent concentration under reduced pressure, freeze-drying, pH adjustment, and adsorption of compound 0406 by bringing the resulting product in contact to carriers such as an anion or cation exchange resin, active charcoal, powder cellulose, silica gel, alumina, and an adsorption resin, to elute the compound from the carrier.

For purification methods, appropriately, use may be made of routine procedures signly or in combination, such as those for antibiotics, for example solvent extraction with water, an organic solvent or a mixture thereof; chromatography; re-crystallization in a single solvent or a mixed solvent.

As has been described above, the purification of compound 0406 is carried out by known methods, but the process may be carried out, for example, as follows.

Firstly, removing the cells by treating the culture by centrifuge or through an MF membrane to adsorb the compound fraction onto a hydrophobic adsorption resin, eluting the adsorbed fraction with methanol, concentrating the eluted fraction under reduced pressure, subjecting further the fraction to silica gel chromatography, thereby adsorbing the fraction onto the silica gel, which is then subjected to step-wise elution process with a chloroform-methanol solution for fractionation, thereafter further fractionating and purifying the fraction by reverse-phase chromatography, the resulting fraction is freeze-dried if necessary.

For administering compound 0406 as a pharmaceutical agent, compound 0406 is advantageously formulated because the compound is water-soluble. Therefore, the compound is administered as it is or is administered as a pharmaceutical composition containing 0.1 to 99.5%, preferably 0.5 to 90% of the compound in a pharmaceutically acceptable inactive carrier with no toxicity.

As such carrier, use may be made of a solid, semi-solid or liquid diluent, a filler and one or more other auxiliary agents. Preferably, the pharmaceutical agent may be administered in the form of a dosage unit. The pharmaceutical composition of the present invention can be administered orally, in the dosage form of intratissue, locally (trans-dermal administration, etc.), or trans-rectally, or the composition may be applied as an external preparation. It is needless to say that the composition should be administered in dosage forms appropriate for these administration.

The dose as an immuno suppressive agent is preferably adjusted, taking into considerations the conditions of a patient, such as age and body weight, administration route, and the nature and severity of the disease, but generally, the dose is within a range of 10 to 200 mg of the effective component per day for adults in accordance with the present invention. In some case, the dose may satisfactorily be more than that or less than that. For a higher dose, the dose should preferably be divided.

The oral administration may be carried out at a dosage unit in solids or liquids, for example a powder formulation, a powdery mixture formulation, a tablet, a sugar-coated formulation, a capsule, a drop, a sub-lingual tablet and other formulations.

Such powder formulation can be prepared by pulverizing the active substance at appropriate fineness. Such powdery mixture formulation may be prepared by pulverizing the active substance at appropriate fineness, thereafter mixing the resulting pulverized substance with a similarly pulverized pharmaceutical carrier such as starch, edible carbohydrates such as mannitol, and others. If necessary, a flavoring agent, a preservative, a dispersing agent, a coloring agent, a fragrance and the like may be mixed with these formulations.

Such capsule may be produced by pulverizing or granulating the substance into a powder formulation or a powdery formulation or a granule formulation, and filling these formulations into an encapsulating coating such as gelatin capsule. A lubricating agent or a fluidizing agent, for example colloidal silica, talc, magnesium stearate, calcium stearate, and solid polyethylene glycol, may be mixed with those in powdery forms, followed by filling procedure. The addition of a disintegrator or a solubilizing agent, for example carboxymethyl cellulose, calcium carbonate, and sodium carbonate, may improve the pharmaceutical efficacy of the resulting capsule when administered.

The micro-fine powder of the product is suspended and dispersed in vegetable oil, polyethylene glycol, glycerin or a surfactant, which is then covered with a gelatin sheet to prepare a soft capsule.

Such tablet may be prepared by preparing a powder mixture, granulating or slugging the mixture, and subsequently adding a disintegrator or a lubricating agent to the mixture, followed by tableting.

As to such powder mixture, the substance appropriately pulverized may satisfactorily be mixed with a diluent described above or a base; if necessary, the powder mixture may be used in combination with a binder (for example, sodium carboxymethyl cellulose, alginate salt, gelatin, polyvinyl pyrrolidone, polyvinyl alcohol ), a sustained-release promoting agent (for example, paraffin), a re-absorption agent (for example, quarternary salt) and/or an adsorption agent (for example, bentonite, kaolin, dicalcium phosphate). Firstly, the powder mixture may be wetted with a binder such as syrup, starch paste, gum arabic, a cellulose solution or a polymer solution, and subsequently, the resulting mixture may be forced through a sieve for granulation. Instead of granulation of the powder in such manner, the powder is firstly subjected to a tableting machine, and the resulting slug in an incomplete form is pulverized into granules.

To the granules thus prepared may be added a lubricating agent such as stearic acid, stearate salt, talc, mineral oil and others, to prevent the sticking of the granules to each other. The thus lubricated mixture is then tableted. The pharmaceutical agent may be bonded with an inactive fluid carrier, without passing through any process of granulation or slugging, followed by direct tableting. A transparent or opaque protective coating comprising a sealed Shellac coating, a coating of sugar or a polymer material, and a polished coating of wax, may be used satisfactorily.

Other oral dosage forms for example liquid, syrup, and elixir, may be prepared at a dosage unit containing a given amount of the compound. Such syrup may be prepared by solubilizing the compound into an aqueous solution with appropriate flavor; such elixir is formulated by dispersing the compound in an alcoholic carrier with no toxicity. If necessary, a solubilizing agent or an emulsifying agent (for example, ethoxylated isostearyl alcohols, polyoxyethylene sorbitol esters), preservative, a flavoring agent (for example, peppermint oil and saccharin) and others may be added as well.

If necessary, the dosage unit formulation for oral administration may satisfactorily be prepared in a microcapsule. By coating the formulation or embedding the formulation into a polymer or wax, the prolongation of the duration of the action or the sustained release may be realized.

Parenteral administration may be carried out by using a liquid dosage unit for subcutaneous, intramuscular or intravenous injections, for example a liquid or suspension formulation. These formulations are prepared by suspending or solubilizing a given amount of the compound in a liquid carrier with no toxicity, suitable for the purpose of injections; for example, these formulations may be prepared by suspending or solubilizing the compound in an aqueous or oily medium and subsequently sterilizing the suspension or the solution. Otherwise, a given amount of the compound is placed in a vial, followed by sterilization of the contents together with the vial, which is then sealed. For dissolution or mixing immediately before administration, a spare vial or a spare carrier may be prepared preliminarily together with the powdery or freeze-dried effective component. So as to prepare isotonic injections, non-toxic salts or salt solutions may be added satisfactorily. Additionally, a stabilizer, a preservative or an emulsifier and the like may be used in combination.

Rectal administration may be carried out by using a suppository prepared by mixing the compound with a low-melting solid, for example polyethylene glycol, cacao fat, higher esters (for example, myristyl palmitate) and mixtures thereof.

The present invention will now be described in examples, but the invention is not limited to these examples.

EXAMPLE 1

(1) Fermentation

A base medium (10 ml) comprising 2% glycerol, 1% polypeptone (manufactured by Nippon Seiyaku Co., Ltd.), and 0.5% tuna meat extract, pH 7.0 was poured into a 50-ml Erlenmeyer flask, into which *Nocardia brasiliensis* IFM 0406 (FERM BP-5498) was inoculated for culturing with shaking at 30° C. for 72 hours. Furthermore, the seed culture was then inoculated at 1% v/v in 1.5 liters of the same medium poured in a 5-liter flask. In the same manner, preliminary culturing was carried out. The pre-culture broth was then inoculated in a 200-liter tank containing 150 liters of the same medium for culturing at a 150-liter aeration volume per minute and an agitation of 200 rpm at 30° C. for 90 hours.

(2) Recovery and Purification

For sterilization, the resulting culture of 150 liters was then filtered through a membrane with a pore size of 0.45 $\mu$m (Pericon cassette system manufactured by Milli-pore, Co. Ltd.). The filtrate fraction was adsorbed onto a Dia-ion HP 20 column (manufactured by Mitsubishi Plastics Industries, Ltd.) of 15×100 cm and sufficiently washed in 50% methanol to remove contaminants off, followed by elution with 20 liters of methanol. Because compound 0406 exerted specific inhibition activity against *Aspergillus niger* (minimum inhibitory concentration of 25 $\mu$g/ml), the compound in the eluted fraction was detected by means of, as a marker, the growth inhibitory activity against a subjective fungus *A. niger* on a Sabouraud dextrose agar medium by a paper disk method.

The eluted fraction was concentrated into one liter in vacuo. The concentrated solution was adsorbed onto a silica gel column (5 cm×50 cm), which was then eluted with each 4 liters of mixtures of chloroform:methanol:water (=(a) 4:1:0, (b)1:1:0 and (c)1.5:1:0.1).

Individual fractions from (a), (b) and (c) were further fractionated and purified by HPLC (high-performance liquid chromatography). For HPLC fractionation and purification, Capcell Pack C18 SG120 column (manufactured by Shiseido Co., Ltd.) of 5×250 mm was used. The individual fractions were adsorbed onto the column, followed by gradient elution with 20–50% acetonitrile. Ten milliliters were collected as one fraction per tube. Using as the marker the growth inhibitory activity against *A. niger*, active fractions were collected.

Freeze-drying and collecting individual active fractions, purified products were recovered as 0406-A (2 g), B (150 mg), C (300 mg), D (200 mg), E (25 mg) and F (15 mg). For example, 0406-A was white powder, having the structural formula and physico-chemical properties as shown above and also having an immuno suppressive action. Comparing 0406-A with known substances and known antibiotics, all having immuno suppressive actions, 0406-A was identified as a novel substance because none of the other substances has the same structural formula.

EXAMPLE 2

The in vitro immuno suppressive activity in murine mixed lymphocyte reaction is measured by as T-cell growth inhibitory activity.

(1) Sample Preparation

The HPLC-purified 0406-A was solubilized at a concentration of 1 mg/ml in sterilized water.

(2) Assay

The murine mixed lymphocyte reaction (MLR) was carried out by using T cells from C57BL/6 (H-$2^b$) splenocytes as responder cells and mitomycin C-treated BALB/C (H-$2^d$) splenocytes as stimulator cells and mixing and culturing them together.

The responder cells were prepared as follows. Spleen was resected from C57BL/6 mice (5 to 6 weeks old), which was homogenized in an ice-cold RPMI 1640 medium including heat inactivated 10% fetal calf serum and filtered through a gause piece, to recover a single-cell suspension.

After recovery with centrifuge, the suspension was treated with an ammonium chloride solution at 4° C. for one minute to remove erythrocyte cells contaminated therein. Centrifuging to recover a splenocyte suspension, subsequent T-cell separation was carried out by using a large murine T-cell enrichment column (manufactured by Funakoshi, CO. Ltd.). Centrifuging and washing in the RPMI 1640 medium, the cells were adjusted to $5.6 \times 10^6$ cells/ml in the RPMI 1640 medium containing 50 $\mu$M 2-mercaptoethanol and 10% FCS to prepare a suspension of the responder cells.

The stimulator cells were prepared by resecting spleen from BALB/C mice (5 to 6 weeks old), preparing a splenocyte suspension in the same manner, and treating the suspension in mitomycin C of 50 $\mu$g/ml at 37° C. for 30 minutes. After washing three times by centrifugation, the cells were resuspended and adjusted to $5.6 \times 10^6$ cells/ml in the RPMI 1640 medium containing 50 $\mu$M 2-mercaptoethanol and 10% FCS to prepare a stimulator cell suspension.

The responder cells (90 $\mu$l), the stimulator cells (90 $\mu$l) and a sample solution (20 $\mu$l) were added into a 96-well round-bottom microtiter plate, for culturing at 37° C. under conditions of 5% $CO_2$-95% air for 96 hours. Blast formation of T cells was determined on the basis of the uptake of tritium-labeled thymidine. After 96-hour culturing, the cells were pulse-labeled at 0.5 $\mu$Ci/well by addition of the tritium-labeled thymidine. After additional incubation for 7 hours, the culture was collected on a glass fiber filter paper by using a multiple sample collector. The radioactivity on the filter paper disk corresponding to each well was measured by liquid scintillation assay (Beta Counter). The count of each well was measured in repetition and then averaged to calculate a count per minute (cpm). The extent of the inhibition of the tritium-labeled thymidine uptake (blast formation) was consequently shown in the form of $IC_{50}$ in Table 6. As controls, the $IC_{50}$ of Ascomycin, Cyclosporin A, and Rapamycin are shown together.

TABLE 6

Effects of immuno suppressive agents on MLR

| Compound | $IC_{50}$ ($\mu$g/ml) |
|---|---|
| 0406-A | 0.16 |
| Ascomycin | 0.008 |
| Cyclosporin A | 0.01 |
| Rabamycin | <0.001 |

EXAMPLE 3

(1) The cytotoxity test of compound 0406-A shown in Example 1 was carried out against cultured cell lines. The results are shown in Table 7.

TABLE 7

Cytotoxity test

| | $IC_{50}$ ($\mu$g/ml) | | |
|---|---|---|---|
| Cell lines | 0406-A | Cyclosporin A | Ascomycin |
| HEK-297 | >100 | <6 | 25 |
| Cos-1 | >100 | <6 | 58 |
| YAC-1 | >100 | <6 | 50 |
| HeLa | >100 | 12 | 13 |

Cell suspensions ($5.6 \times 10^4$ cells/ml) were prepared by using the Minimum Essential Medium (MEM)-Dulbecco's medium for HEK-297, Cos-1, and Hela cells, and the RPMI 1640 medium for YAC-1 cells (all media containing 10% bovine serum). Samples (0406A, Cyclosporin and Ascomycin) were prepared by serial two-fold dilution starting from 1 mg/ml, by using the individual media. A cell suspension (180 $\mu$l) and a sample solution (20 $\mu$l) were added into each well of a 96-well microtiter plate, for culturing at 37° C. in wet 5% $CO_2$-95% air environment. After culturing for 96 hours, $^3$H-thymidine (0.5 $\mu$Ci/well) was added into each well. The microtiter plate was incubated for 4 hours, followed by trypsin treatment of the cell lines excluding YAC-1, and the resulting cells were recovered on glass fiber filters to measure the radioactivity incorporated into the cells by means of a liquid scintillation counter. From the radioactivity (c) of a well with no addition of any sample and the radioactivity (t) of each of the wells with addition of the individual samples, the growth inhibition rate was determined by the formula (100-t)/c$\times$100 (%). $IC_{50}$ was calculated from the results.

It was confirmed that the cytotoxity level of compound 0406-A of the present invention was lower than that of the commercially available immuno suppressive agents.

(2) In vitro cytotoxic T-cell activity (CTL: cytotoxic T-cell) (Inhibitory effect on CTL generation, induced by murine mixed lymphocyte reaction)

A suspension solution ($5.5 \times 10^6$ cells/ml; 0.9 ml) of BALB/C (H-$2^d$) splenocytes prepared in the same manner as in Example 2, a suspension solution ($5.5 \times 10^6$ cells/ml; 0.9 ml) of C57BL/6 (H-$2^b$) splenocytes preliminarily treated with mitomycin C, and a sample solution (0.2 ml) were added into a 24-well multi-dish, for culturing at 37° C. under conditions of 5% $CO_2$-95% air for 5 days. After completion of cultivation, the cells were recovered by centrifuge, which were then suspended in the RPMI 1640 medium containing 10% bovine serum, for use as the effector cells.

EL-4 cells (H-$2^b$) were used as the target cells. The incubation of the EL-4 cells ($10^6$) with 0.1 $\mu$Ci Na$_2^{51}$CrO$_4$ at 37° C. for 3 hours promoted the $^{51}$Cr uptake in the cells, and subsequently, the cells were washed and the concentration was adjusted to $2 \times 10^5$ cells/ml for use as the target cells.

The determination of the cytotoxic T-cell generation was carried out as follows. The effector cell suspension (100 $\mu$l) and the target cell suspension (100 $\mu$l) were added into a 96-well round-bottom microtiter plate for cultivation at 37° C. for 4 hours, to measure $^{51}$Cr release in the supernatant. Then, the cytotoxic T-cell activity was calculated by the formulated below.

Cytotoxic T-cell activity =
[radioactivity of (effector cell + target cell)] −

-continued

| |
|---|
| (radioactivity of target cell alone)/ (radioactivity of target cell treated with 0.1N HCl) − (radioactivity of target cell alone) × 100 |

The activity of the cytotoxic T cell was represented in lytic unit (LU). The activity in LU was represented per $10^7$ effector cells, when 1 LU was designated as the number of effector cells required for 20% lysis of the $2\times10^4$ target cells. The results are shown in the following Table 8. As apparently shown in the results, it was confirmed that compound 0406-A decreased the induction of CTL in a dose-dependent manner.

TABLE 8

| Compound | Concentration (ng/ml) | Cytotoxic T-cell activity (u) | Inhibition rate (%) |
|---|---|---|---|
| 0406-A | 10,000 | <0.1 | >99.5 |
| | 2,500 | 0.1 | 99.5 |
| | 625 | 12.5 | 39.5 |
| | 126 | 22.0 | 0 |

EXAMPLE 4

Using starting materials as shown below, a tablet was prepared;

(1) the substance prepared in Example A, namely 0406-A; 20 g (2) lactose; 80 g (3) corn starch; 30 g (4) magnesium stearate; 2 g.

More specifically, the substances (1), (2), and (3) of 15 g, were mixed together and granulated together with a paste prepared from (3) of 10 g. To the resulting granule were added and mixed thoroughly the substances (3) of 5 g and (4), and the resulting mixture was then compressed by means of a compression tableting machine, to prepare 800 tablets each containing 25 mg of the effective component (1) per tablet.

Effects of the Invention

The present invention is to provide compound 0406, a novel compound having superior biological activity for use in a variety of pharmaceutical products as an immuno suppressive agent and the like.

What is claimed is:

1. A biologically pure or isolated *Nocardia brasiliensis* capable of producing compound 0406 of the formula (1)

(1)

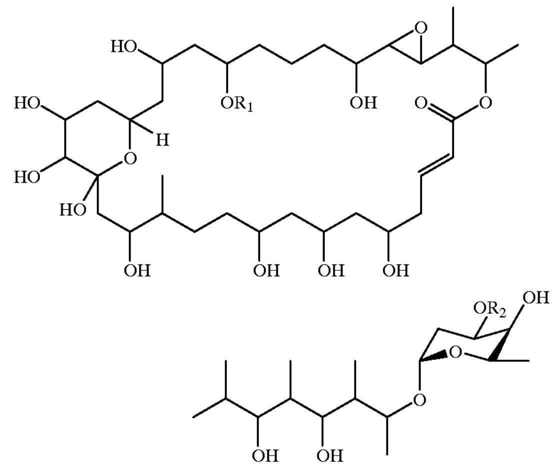

wherein $R_1$ is $—COCH_2COOH$ or H; $R_2$ is $—CO(CH_2)_3CH_3$ or $—CO(CH_2)_4CH_3$ or H, or a pharmaceutically acceptable salt thereof.

2. The *Nocardia brasiliensis* of claim 1 capable of producing compound 0406-A, wherein $R_1$ is $—COCH_2COOH$ and $R_2$ is $—CO(CH_2)_3CH_3$.

3. The *Nocardia brasiliensis* of claim 1 capable of producing compound 0406-B, wherein $R_1$ is $—COCH_2COOH$ and $R_2$ is H.

4. The *Nocardia brasiliensis* of claim 1 capable of producing compound 0406-C, wherein $R_1$ is H and $R_2$ is $—CO(CH_2)_3CH_3$.

5. The *Nocardia brasiliensis* of claim 1 capable of producing compound 0406-D, wherein $R_1$ is H and $R_2$ is H.

6. The *Nocardia brasiliensis* of claim 1 capable of producing compound 0406-E, wherein $R_1$ is $—COCH_2COOH$ and $R_2$ is $—CO(CH_2)_4CH_3$.

7. The *Nocardia brasiliensis* of claim 1 capable of producing compound 0406-F, wherein $R_1$ is H and $R_2$ is $—CO(CH_2)_4CH_3$.

8. A *Nocardia brasiliensis* according to claim 1 which is *Nocardia brasiliensis* IFM 0406 (FERM BP-5498).

* * * * *